(12) United States Patent
Groenewegen (10) Patent No.: US 6,556,860 B1
(45) Date of Patent: Apr. 29, 2003

(54) SYSTEM AND METHOD FOR DEVELOPING A DATABASE OF BODY SURFACE ECG FLUTTER WAVE DATA MAPS FOR CLASSIFICATION OF ATRIAL FLUTTER

(75) Inventor: Arne Sippens Groenewegen, Burlingame, CA (US)

(73) Assignee: The Regents of the University of California, Oakland, CA (US)

( * ) Notice: Subject to any disclaimer, the term of this patent is extended or adjusted under 35 U.S.C. 154(b) by 175 days.

(21) Appl. No.: 09/724,947

(22) Filed: Nov. 28, 2000

Related U.S. Application Data
(60) Provisional application No. 60/189,513, filed on Mar. 15, 2000, provisional application No. 60/196,204, filed on Apr. 11, 2000, and provisional application No. 60/189,611, filed on Mar. 15, 2000.

(51) Int. Cl.⁷ ............................................. A61B 5/042
(52) U.S. Cl. ..................................................... 600/509
(58) Field of Search ................................. 128/897–898, 128/901, 920, 923; 600/509, 515, 518

(56) References Cited

U.S. PATENT DOCUMENTS

| | | | |
|---|---|---|---|
| 4,550,502 A | 11/1985 | Grayzel | 33/1 B |
| 4,721,114 A | 1/1988 | Dufault et al. | 128/696 |
| 5,313,953 A | 5/1994 | Yomtov et al. | 128/696 |
| 5,609,158 A | 3/1997 | Chan | 128/705 |
| 5,818,570 A | 10/1998 | Urbanczyk | 355/75 |
| 5,840,038 A | 11/1998 | Xue et al. | 600/512 |
| 6,038,476 A | 3/2000 | Schwartz | 607/27 |
| 6,064,906 A * | 5/2000 | Langberg et al. | 600/518 |
| 6,178,347 B1 * | 1/2001 | Olsson | 600/518 |

* cited by examiner

Primary Examiner—Kennedy Schaetzle
Assistant Examiner—Kristen Droesch
(74) Attorney, Agent, or Firm—Lumen Intellectual Property Services, Inc.

(57) ABSTRACT

A method and apparatus for developing a database of mean body surface ECG flutter wave data maps for classification of atrial flutter are described. ECG signals from a plurality of torso sites and multisite endocardial recordings are obtained during CCW and CW typical atrial flutter and atypical atrial flutter. Flutter wave episodes are divided into two or three successive time intervals showing stable potential distributions from which data maps are computed. Body surface mapping of CCW and CW typical atrial flutter and atypical atrial flutter is compared with endocardial activation sequence mapping to confirm validity between the body surface ECG pattern and the underlying right or left atrial activation sequence. The body surface ECG map patterns of CCW and CW typical atrial flutter are characterized by a stereotypical spatial voltage distribution that can be directly related to the underlying activation sequence and are highly specific to the direction of flutter wave rotation. The mean body surface ECG flutter wave data maps present a unique reference database for improved clinical detection and classification of typical and atypical atrial flutter.

54 Claims, 10 Drawing Sheets

Flutter Wave Integral

SYSTEM AND METHOD FOR DEVELOPING A DATABASE OF BODY SURFACE ECG FLUTTER WAVE DATA MAPS FOR CLASSIFICATION OF ATRIAL FLUTTER

CROSS-REFERENCE TO RELATED APPLICATIONS

This application is cross-referenced to and claims priority from co-pending provisional U.S. patent application No. 60/189,513, filed Mar. 15, 2000, provisional U.S. patent application No. 60/196,204 filed on Apr. 11, 2000, and provisional U.S. patent application No. 60/189,611, filed on Mar. 15, 2000, all of which are incorporated herein by reference.

STATEMENT REGARDING FEDERALLY SPONSORED RESEARCH OR DEVELOPMENT

This invention was supported in part by grants from the National Institutes of Health HL09602 and R01-HL55027. The Government has certain rights in the invention.

FIELD OF THE INVENTION

This invention relates generally to a method for classification of atrial arrhythmias. More particularly, it relates to a system for developing a database of body surface ECG flutter wave maps for the classification of the type and rotation of atrial flutter.

BACKGROUND ART

Clinical electrocardiography of counterclockwise (CCW) typical atrial flutter (also known as common or type I atrial flutter) dates back to the early part of the $20^{th}$ century. The continuous or "sawtooth" pattern of the flutter wave in standard ECG leads II and III was first reported and attributed to an atrial impulse circulating around both caval veins. Later reports provided further evidence to the concept of an excitation wave rotating in a CCW direction in the right atrium and giving rise to the distinct "sawtooth" pattern with predominantly negative flutter waves in the inferior leads and $V_6$ combined with a positive flutter wave in $V_1$. With the introduction of multisite endocardial mapping, entrainment techniques, and catheter ablative strategies in the therapeutic management of the typical form of atrial flutter, flutter wave propagation has been convincingly demonstrated to occur in a macroreentrant right atrial circuit confined anteriorly by the tricuspid annulus and posteriorly by the crista terminalis and its inferior extension the eustachian ridge, which act as natural barriers to conduction. In addition to CCW rotation of the flutter wave, it has been shown that clockwise (CW) impulse rotation in the same right atrial circuit can be frequently observed. Although there is general consensus on the previously mentioned distinct morphology of the standard 12-lead electrocardiogram (ECG) during CCW typical atrial flutter, ECG features found to be most specific for CW typical atrial flutter are more variable. Visual assessment of the flutter wave polarity on the standard 12-lead ECG is hampered by low voltage, a continuously undulating signal, and QRST wave obscurement when a low degree of atrioventricular (AV) block is present. Moreover, the standard 12-lead ECG has been found insufficient in distinguishing between CCW and CW typical atrial flutter or between the two forms of typical and atypical atrial flutter.

Consequently, electrocardiographic determination of the type (typical or atypical) and rotation (CCW or CW for typical) of atrial flutter is often hampered by inaccurate and inconclusive scalar waveform analysis of the standard 12-lead ECG. This may then require more invasive techniques being employed to obtain further information or a misdiagnosis may occur, both of which increase patient risk and expense. Such additional information may be needed to select an appropriate therapy, e.g., radiofrequency catheter ablation, or anti-arrhythmic drugs.

There is a need, therefore, for an improved ability to discriminate the type and rotation of atrial flutter.

OBJECTS AND ADVANTAGES

Accordingly, it is a primary object of the present invention to provide a system for developing a database of body surface ECG flutter wave data maps. It is a further object of the invention to provide an apparatus for classifying typical and atypical atrial flutter for said database. It is an additional object of the invention to provide a method of storing a database of mean body surface ECG flutter wave data map patterns in a computer-readable medium for retrieval, analysis and sharing. The database will then contain data maps for comparison to patient body surface ECG flutter wave data maps to improve detection and classification of atrial flutter.

SUMMARY

The aforementioned objects and advantages are attained by developing a database of body surface ECG flutter wave data maps for classification of typical or atypical atrial flutter. The present invention also includes a method and apparatus for generating the database. The method generally comprises generating atrial flutter data in a subject; receiving the atrial flutter data from the subject; classifying the data as typical clockwise (CW) or counterclockwise (CCW) and atypical atrial flutter; averaging the classified data obtained from one or more subjects; and storing and accessing the averaged data in the database. The flutter wave data may be in the form of data maps such as flutter wave potential maps or flutter wave integral maps. The maps are classified as being characteristic body surface maps specific to CCW or CW typical or atypical atrial flutter data. The atrial flutter may be induced in the subject by electrically stimulating the arrhythmogenic substrate of the atrium using a probe. The data may be verified before averaging. The mean maps may then be calculated from verified atrial flutter wave maps to construct a database of characteristic body surface ECG flutter wave maps.

The mean flutter wave maps in the database can be used to automatically characterize flutter wave data from a patient as being typical CW, typical CCW or atypical atrial flutter.

DETAILED DESCRIPTION

Although the following detailed description contains many specifics for the purposes of illustration, anyone of ordinary skill in the art will appreciate that many variations and alterations to the following details are within the scope of the invention. Accordingly, the following embodiments of the invention is set forth without any loss of generality to, and without imposing limitations upon, the claimed invention.

Body surface ECG mapping can be applied to improve detection of typical atrial flutter or to optimize electrocardiographic characterization of the flutter circuit location. The use of body surface mapping allows ECG data presentation in a unique spatial format that contains a display of the complete CCW and CW flutter wave distribution on the human torso surface. This display format provides a more realistic reflection of the complex pattern of flutter wave propagation in the right and left atrium.

The embodiments of this invention relate to developing a database of mean CCW and CW typical multi-lead body surface flutter wave data map patterns that can be used to detect and classify typical or atypical atrial flutter. The database enables more sophisticated and less ambiguous clinical classification of the flutter type and its direction of rotation than currently feasible with the existing algorithms based on scalar features of the standard 12-lead ECG. The database may be particularly useful in the clinical scenario where typical atrial flutter may not be recognized and considered for catheter ablative therapy because the 12-lead ECG pattern during CW or CCW flutter is not "close to classic." The use of a higher number of leads than the standard 12 leads may be beneficial in improving diagnosis and noninvasive electrocardiographic evaluation of atrial flutter.

Alternatively, the database may be useful when the 12-lead ECG pattern of a truly atypical atrial flutter may be mistakenly labeled as a typical flutter that would be amenable for ablation. Clinical application of the database of mean CCW and CW typical flutter wave data maps may also lead to improved noninvasive methods of patient selection so that treatment strategies can be better tailored regarding the optimal choice of therapy before invasive electrophysiologic studies are carried out. In addition, techniques similar to the ones described in this invention may be adopted to develop novel databases of body surface ECG flutter wave, e.g., integral or potential, map patterns that are specific to atypical atrial flutter (i.e. non-isthmus dependent right atrial flutter or left atrial flutter).

Figure 1:
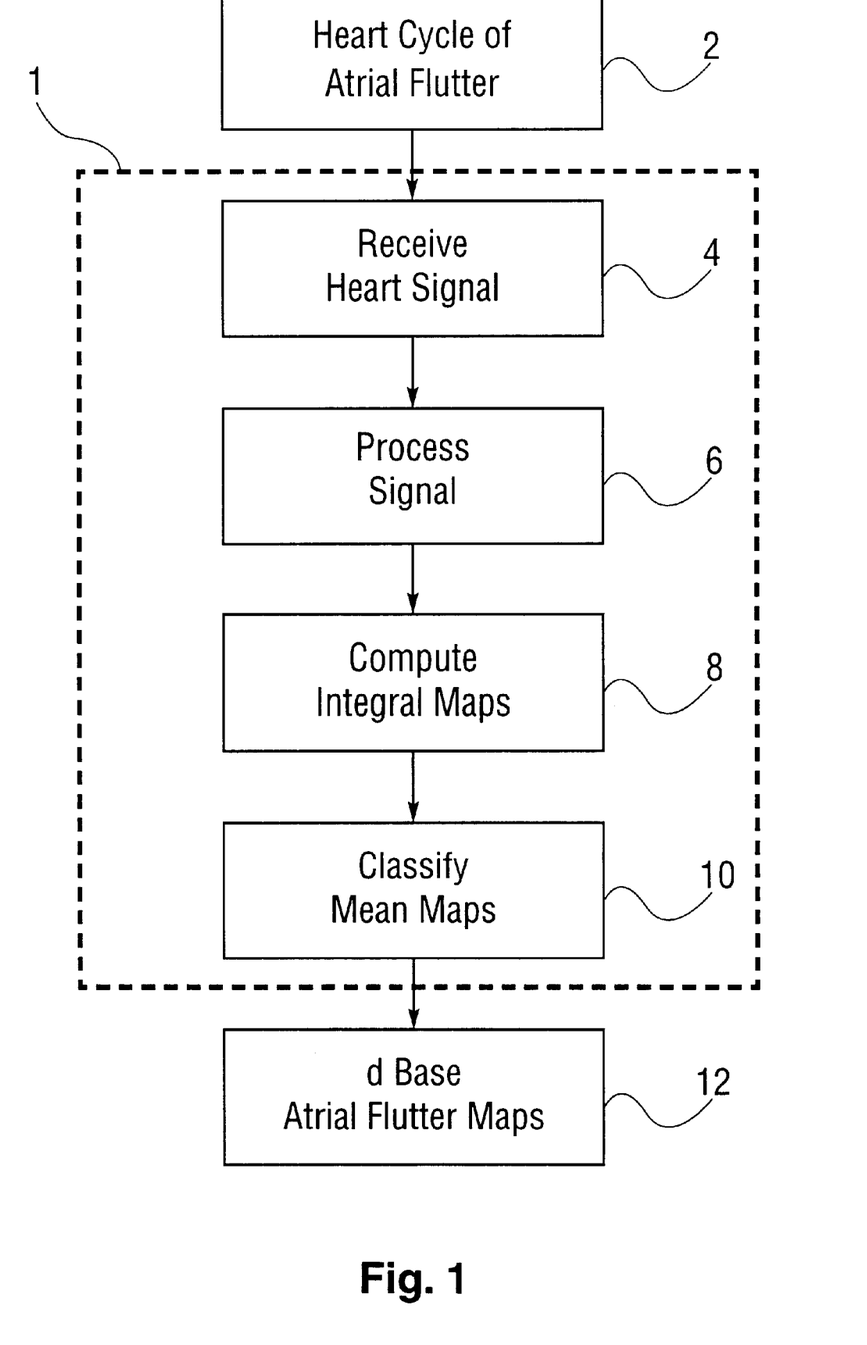
FIG. 1 depicts an overview of the development of a database of mean body surface ECG map patterns for classification of atrial flutter according to an embodiment of the present invention.

The method of the present invention is illustrated in the simplified flow diagram of FIG. 1. The electrical signal from a heart cycle for atrial flutter 2 is spontaneous or it can be induced. The heart signal is received 4 as unipolar or bipolar ECG signals simultaneously obtained from an array of multiple electrodes on predetermined torso sites. During signal processing 6, leads with inferior signal quality are rejected and baseline adjustment is performed by linear interpolation. A series of potential maps of the entire flutter wave cycle is computed at 2-ms intervals (other intervals can be used). Flutter wave onset and offset are determined, e.g., at the time instant when a peak reference voltage, e.g., 30 $\mu$V is reached and when the peak voltage drops below the reference voltage, respectively. Subsequently, body surface ECG flutter wave maps are computed 8 over selected time intervals where stable voltage distributions occur for a time interval of at least 20 ms. In addition, mean maps are calculated of typical (CCW and CW) and atypical flutter wave data maps obtained in different patients to document their distinct surface map morphology. Quantitative data classification is carried out by subjecting the flutter wave maps to a mathematical analysis using correlation coefficients 10. The mean flutter wave maps of typical (CCW and CW) and atypical body surface ECG atrial flutter are stored in a database 12. This unique database will then contain mean body surface flutter wave maps for comparison to patient body surface ECG flutter wave data maps to improve detection and classification of atrial flutter. The maps in the database provide a useful reference for characterizing flutter wave data from a patient. By comparing patient data to the maps in the database, a physician can provide a better diagnosis and make better decisions for a treatment regimen for an individual patient. Maps of the selected time intervals can be represented, for example, as potential maps or integral maps. In a potential map, the signal sensed by sensors placed on a patient's torso is plotted on a representation of the torso, e.g. as a contour map or color map. In an integral map, the signal sensed by sensors is integrated over some time interval and the integral is plotted on a representation of the torso, e.g. as a contour map or color map.

Figure 2:
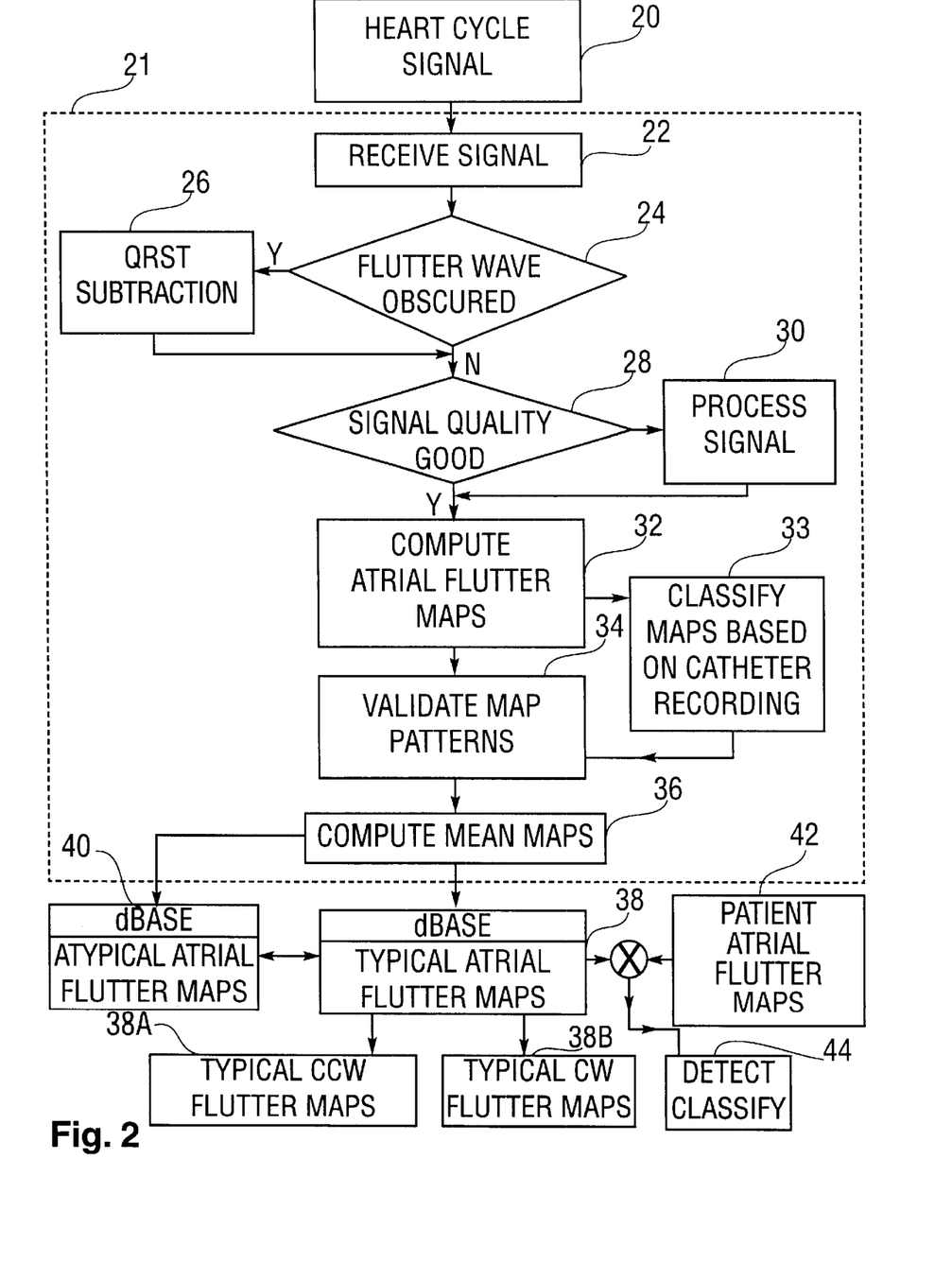
FIG. 2 depicts a system for developing a database of body surface ECG flutter wave data maps for classification of typical and atypical atrial flutter for use to better detect and classify atrial flutter in patients according to an embodiment of the present invention.

Referring to FIG. 2, there is illustrated by means of a more detailed general flow diagram the overall sequence of steps to develop a database of body surface ECG flutter wave data maps for classification of typical or atypical atrial flutter. The electrical heart cycle signal 20 for atrial flutter can be spontaneous or induced. Atrial flutter can be induced by an electric stimulus probe such as a catheter, by pharmacologic, or by other means. The heart cycle signal is processed by a flutter wave classification routine 21.

Figure 5A:
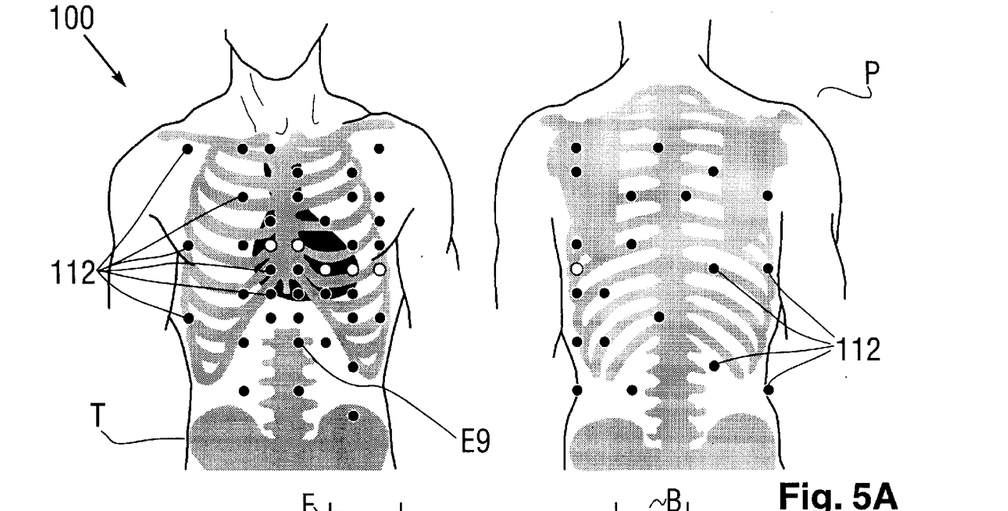
FIG. 5A depicts a sensor system having an array of sensing locations distributed across a subject's torso anatomy according to an embodiment of the present invention.

At step 22, the heart signal is received as unipolar or bipolar ECG signals simultaneously obtained from an electrode array on predetermined torso sites. Referring to FIG. 5A, the techniques of the present invention will generally make use of an array 100 of sensors 112 distributed across anterior and posterior skin surfaces of torso T on patient P. As used herein, proximate means either near or in contact with. Array 100 provides multi-lead ECG data at a plurality of sensing locations distributed across the torso T, typically at over 20 sensing locations, more preferably at over 40 sensing locations, and ideally at 62 or more sensing locations.

Sensors 112 generally comprise unipolar or bipolar electrodes coupled to the patient's skin, or to an alternative accessible body surface (for example via a transesophageal approach) suitable for measuring electrical body surface potential. Suitable electrode structures may include those described in U.S. Pat. Nos. 5,311,873 and 5,634,469, which are incorporated herein by reference. Alternative sensor array structures and associated data acquisition and manipulation components may also be used.

ECG data is preferably acquired simultaneously from each of sensors 112 of array 100 at a sampling rate of over about 500 Hz, ideally at a sampling rate of about 1,000 Hz or more. In some embodiments, sequential sampling of sensors 112 from array 100 may alternatively be used, and higher or lower sampling rates also are feasible. When a lower sampling rate is used, the data may be upsampled using multirate filter banks.

Referring to FIG. 2, at step 24, if the flutter wave is obscured when a low degree of AV block is present, e.g., due to the flutter wave activity coinciding with ventricular recovery of the preceding cardiac cycle, the QRST subtraction 26 routine can be invoked to separate the signals. It may be possible in some circumstances to artificially separate these waves, i.e., by the use of pharmacological compounds that temporarily block AV conduction or by electrical pacing of the ventricle. Alternatively, other signal separation methods and systems may also be used.

Figure 3:
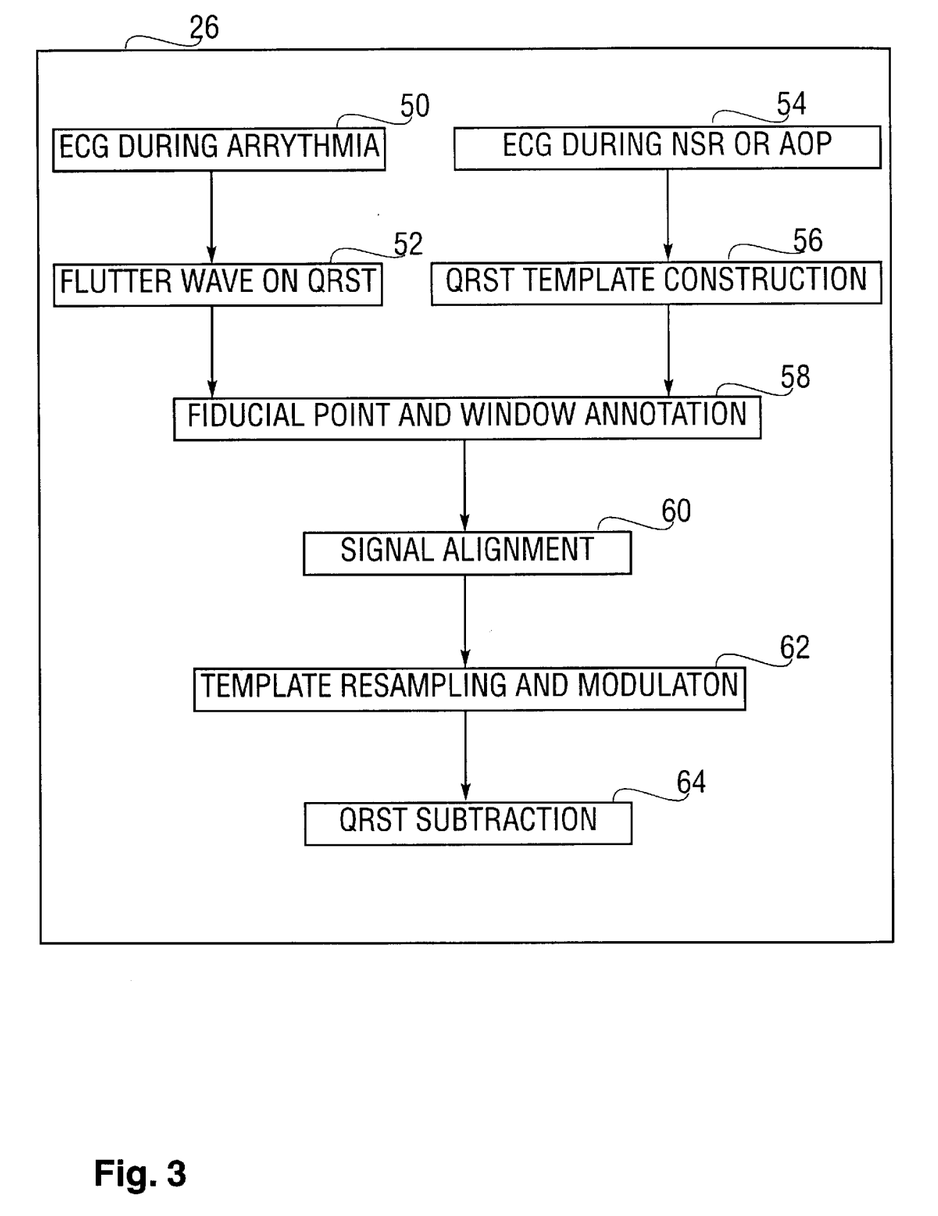
FIG. 3 depicts a method for separating obscured flutter waves from a superimposed QRST complex according to an embodiment of the present invention.

Referring to FIG. 3, the QRST subtraction routine 26 uses an adaptive QRST template constructed from averaged QRST complexes obtained from body surface ECG measurements to enable isolation of the otherwise obscured flutter wave activity.

The method of 26 generally includes recording of unipolar or bipolar ECG data from the array of torso sites in step 50. The measured signal will include both the flutter wave and a superimposed QRST signal portion 52. In the exemplary embodiment, about 100 cardiac cycles of 62-channel unipolar ECG data are measured during normal sinus rhythm (NSR) or atrial overdrive pacing (AOP) 54. Fewer cycles may be used if the spatial and temporal variations of the QRST complex are relatively low. Typically, more than ten cycles will be used, often more than 50 cycles for construction of the QRST template 56.

R wave fiducial points are marked in step 58 and the average R-R interval is computed. The dominant QRS morphology is identified and used to select complexes for template creation. The selection of complexes for template creation 56 may be based on two criteria: QRS pattern and R-R interval length. Each complex that does not have adequate correlation with the template or an R-R duration above the computed threshold is excluded. The R wave fiducial points define a fiducial window in the QRS complexes. The window in the QRS complexes, together with an additional fiducial time window around the peak of the T wave, are annotated, i.e., marked automatically. The fiducial windows are marked in both the QRST template and in a superimposed signal containing a QRST interval together with a superimposed flutter wave.

In step 60, the template 56 and the superimposed signals 52 are aligned. The T wave window is adjusted for each complex based on the QT interval length. After alignment of the fiducial windows, the template is resampled as well as amplitude modulated 62, and then QRST subtraction is carried out 64. Template resampling and modulation are performed to compensate for discrepancies in duration (as a result of rate-related differences in the QRST interval) and amplitude (as a consequence of variations in peak R-T wave voltage, which may be caused by respiratory variation). After the QRST segment is effectively subtracted from each measured signal containing a flutter wave of interest, the morphology of the isolated flutter wave can be analyzed. Further details of QRST subtraction are described in U.S. Provisional Patent Applications Serial Nos. 60/189,513 and 60/189,611, which have been incorporated herein by reference.

Figure 4:
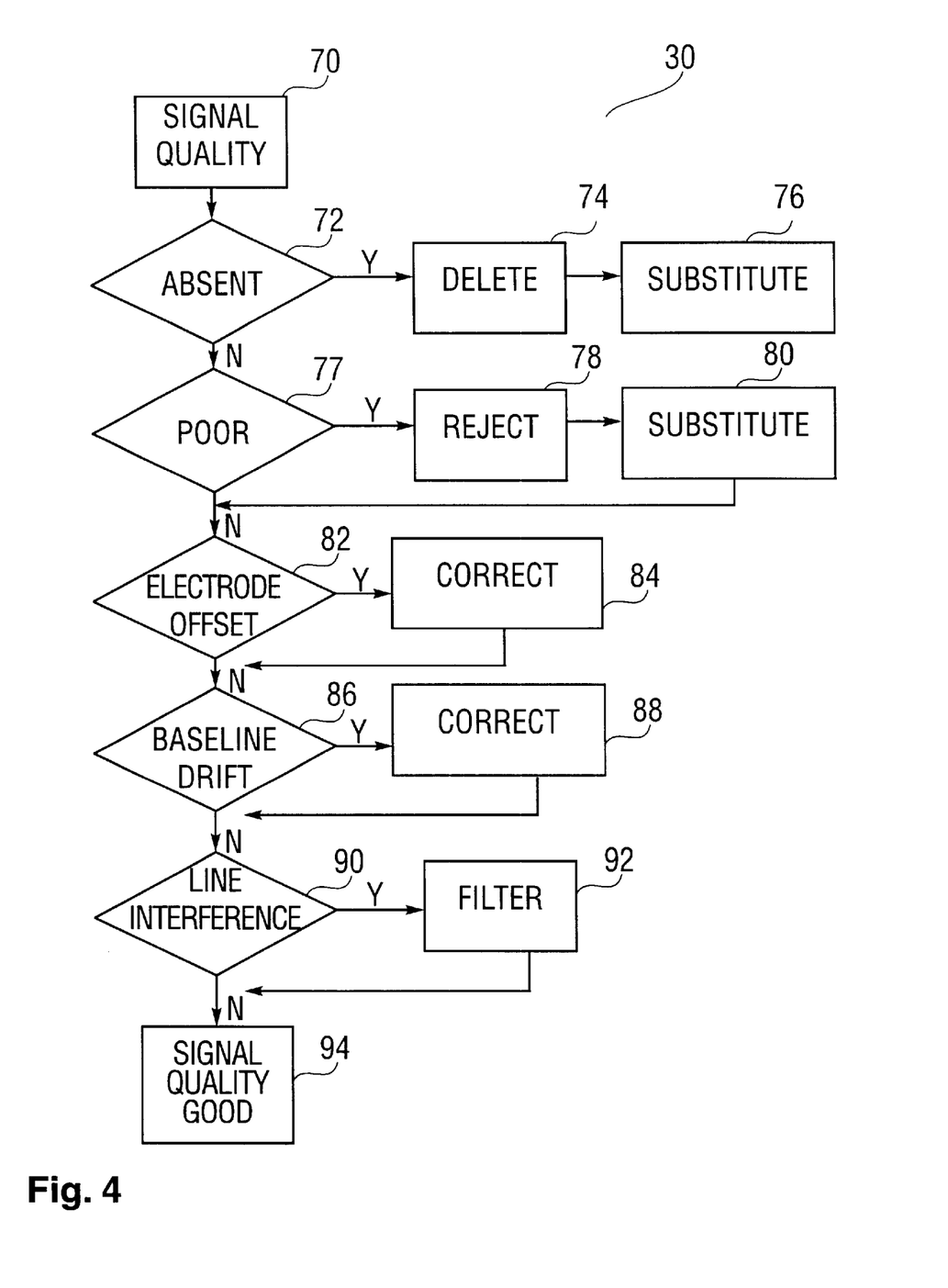
FIG. 4 depicts a method for selecting and processing good quality signals according to an embodiment of the present invention.

Referring to FIG. 2, all lead tracings are visually screened at step 28 in order to reject poor quality signals or signals from lead sites that are obscured by defibrillation patches on the front and back of the subject's chest. The details of the signal-processing step 30 are depicted in the flow diagram of FIG. 4. All lead tracings are visually or automatically screened 70. Absent signals detected 72 are deleted 74 and substitute values 76 are interpolated based on adjoining lead recordings. Poor quality signals detected 77 are rejected 78 and substitute values 80 are interpolated based on adjoining lead recordings. Interelectrode offset differences 82 are corrected 84 and linear baseline drift 86 is corrected 88. Both the offset and drift may be corrected 84, 88 by using linear interpolation after selecting an isoelectric time instant or interval. Due to the absence of a true isoelectric period in the flutter wave cycle, a time instant or interval is selected in the signal near to the zero voltage level directly preceding the negative inscription of the flutter wave. Digital filtering to remove line frequency interference 90 is performed when necessary with a filter 92 such as a 60-Hz notch filter or other type of filter. The end result of the signal processing 30 is a good quality signal 94.

Referring to FIG. 2, by way of example, flutter wave integral maps are computed 32 as follows. Electrocardiographic data is analyzed by inspecting the temporal changes in voltage distribution throughout the flutter wave cycle. Distinct periods within the flutter wave cycle are identified at which stable voltage distributions occur for a time interval of at least 20 ms. Subsequently, integral maps are computed over these selected time intervals with stable voltage distributions.

Figure 5B:
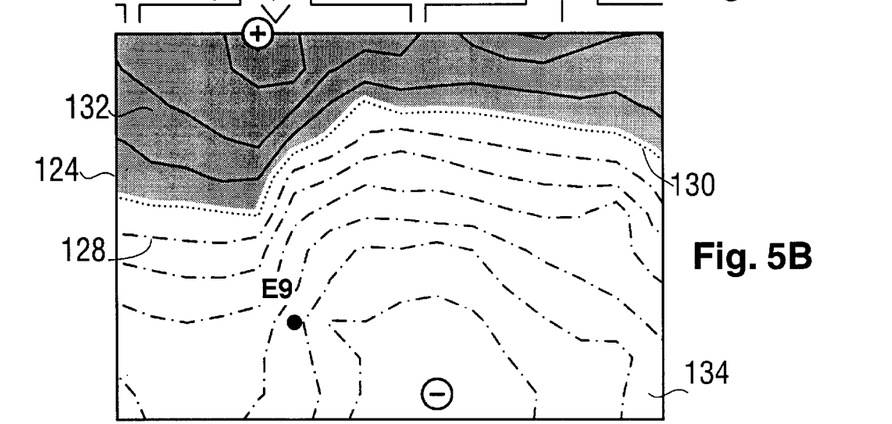
FIG. 5B depicts a body surface flutter wave integral map; a plot of a data matrix generated by mapping the integral values with positions corresponding to the location of the sensors across a subject's torso anatomy according to an embodiment of the present invention.
Figure 5C:
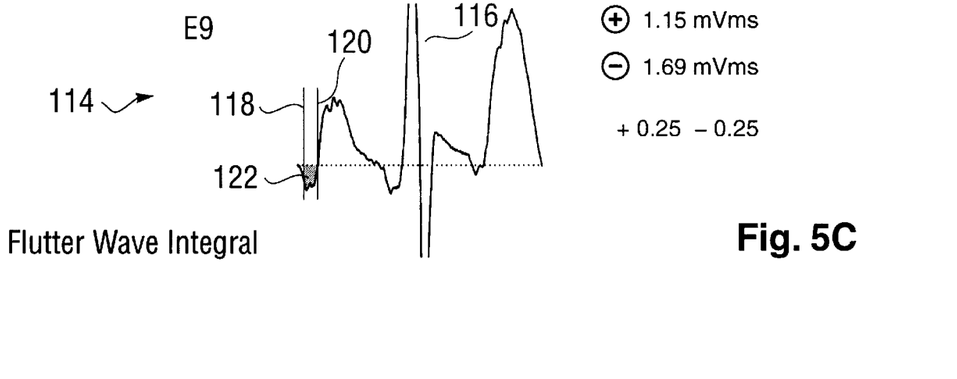
FIG. 5C depicts an ECG trace illustrating a method for calculating an integral value across a selected time interval of a heart signal cycle from a single sensor location according to an embodiment of the present invention.

Referring to FIG. 5C, graph 114 includes an ECG signal tracing 116 representing the variation in voltage over time. Signal tracing 116 may be used to evaluate heart cycle signals. In general, one or more reference heart cycles will be selected for manipulation and comparison. ECG tracing 116 can be used to determine a beginning 118 and end 120 of a time interval 122 of the heart signal cycle that is of interest for evaluating one or more regions of the heart. Alternative criteria for determining flutter wave onset might also be used, and automated detection of one or more time intervals 122 is also feasible. Alternatively, single or multiple time instants in the flutter wave cycle may also be selected.

FIG. 5A depicts a map of sensor locations 112 on the front and back of a subject's torso. FIG. 5B represents a plot of a data matrix generated by mapping the integral values with positions corresponding to the location of the sensors 112 across a subject's torso T in FIG. 5A. FIG. 5C illustrates the calculation of an integral value from a plot 114 of heart cycle signal 116 versus time. In the exemplary embodiment of FIG. 5C, a flutter wave integral numerical value may be calculated based on heart cycle signals 116 within selected time interval 122 having a start time 118 and an ending time 120 for a particular sensor location E9. This calculated flutter wave integral value reflects the time/amplitude area of ECG signal at the sensor location within the selected time interval. Similar integral values are calculated for each sensor location, and the sensor values are mapped within data matrix 124 continuously from a portion of the data matrix associated with a front F of torso T, across a side of the patient P, and to a back B portion of torso T. As shown in FIG. 5B, the data matrix will often be presented graphically by calculating and plotting lines of constant integral values 128 based on the individual discrete integral values and their associated positions within the data matrix. In some embodiments, this information can be summarized by presenting a single line 130 of zero integral value between a region of positive integral values 132 and a region of negative integral values 134. Alternatively, color plots may be used to represent the data matrix wherein different colors represent different integral values or ranges of integral values. Of course, contour maps or color plots of potential values that represent flutter wave data may also be plotted as set forth above.

CCW typical atrial flutter is defined as a right atrial arrhythmia characterized by CCW wavefront rotation around the tricuspid annulus and critical dependence on the subeustachian isthmus. CW typical atrial flutter is defined as a right atrial arrhythmia characterized by CW wavefront rotation around the tricuspid annulus and critical dependence on the subeustachian isthmus.

Referring again to FIG. 2, the atrial flutter wave data maps are classified at step 33 to verify the type of flutter and, if appropriate, sense of rotation. Endocardial multipolar catheter electrogram recordings are obtained from the right atrium, coronary sinus, and possibly the left atrium and are analyzed by determining the activation time in each bipolar lead recording using on-screen digital calipers. These intracardiac recordings are obtained to verify the type of flutter and direction of rotation prior to including the data in the database.

Figure 5D:
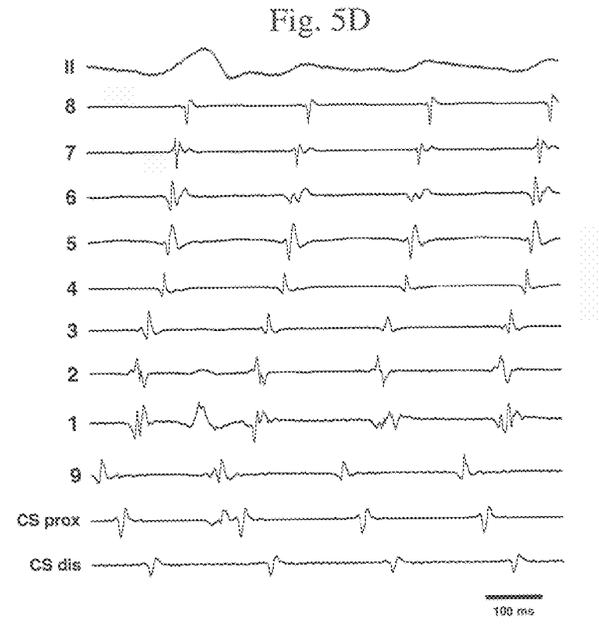
FIG. 5D depicts a series of intracardiac recordings from the right atrium that demonstrate CCW typical atrial flutter.
Figure 5E:
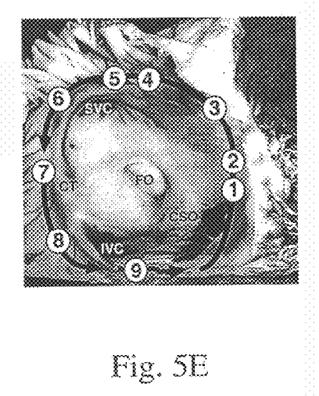
FIG. 5E depicts an endocardial diagram of the right atrium illustrating positions of electrodes for the traces of FIG. 5D.
Figure 5F:
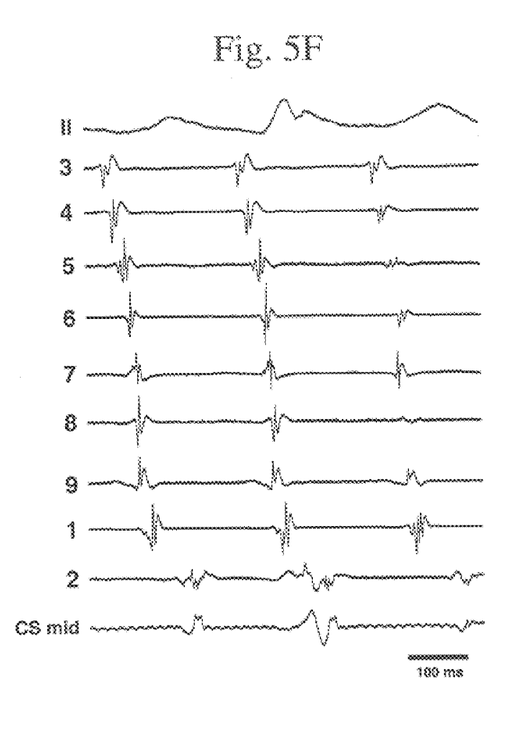
FIG. 5F depicts a series of intracardiac recordings from the right atrium that demonstrate CW typical atrial flutter.
Figure 5G:
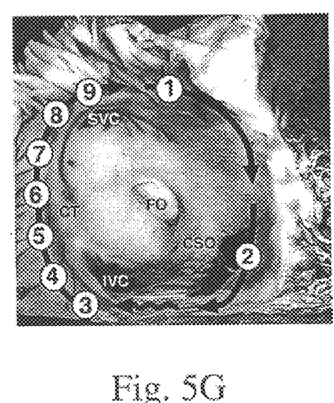
FIG. 5G depicts an endocardial diagram of the right atrium illustrating positions of electrodes for the traces of FIG. 5F.

The difference between CCW and CW atrial flutter wavefront propagation in the right atrium is demonstrated by FIGS. 5D–5G. FIG. 5D depicts surface ECG lead II and intracardiac bipolar catheter electrogram recordings that demonstrate CCW typical atrial flutter. Traces 1 through 9 are numbered in accordance with the temporal sequence of their individual activation times. FIG. 5E depicts an endocardial diagram of the exposed right atrium showing the positions of the corresponding endocardial electrodes for the traces 1 through 9 in FIG. 5D. The remaining two electrograms were recorded at the proximal (prox) and distal (dis) coronary sinus. The endocardial diagram of FIG. 5E also depicts the location of the superior vena cava (SVC) and the inferior vena cava (IVC), crista terminalis (CT), fossa ovalis (FO), and the coronary sinus os (CSO), and features the CCW direction of impulse propagation, as shown by the arrows in FIG. 5E, in the macroreentrant right atrial circuit. In a similar fashion, FIGS. 5F and 5G respectively depict electrograms and endocardial electrode positions that demonstrate typical CW atrial flutter. Similar data can be obtained to verify the presence of atypical atrial flutter. CS mid in FIG. 5F refers to the middle part of the coronary sinus.

Referring to FIG. 2, at step 34, quantitative data evaluation is carried out by subjecting the integral maps to a mathematical analysis using correlation coefficients in order to: 1) compare the intrapatient variability of the flutter wave pattern obtained at various periods of the flutter wave cycle, and 2) assess the interpatient comparability of typical flutter wave patterns with the same direction of rotation. Similar quantitative data evaluation can be applied to analyze atypical flutter wave patterns.

Figure 6:
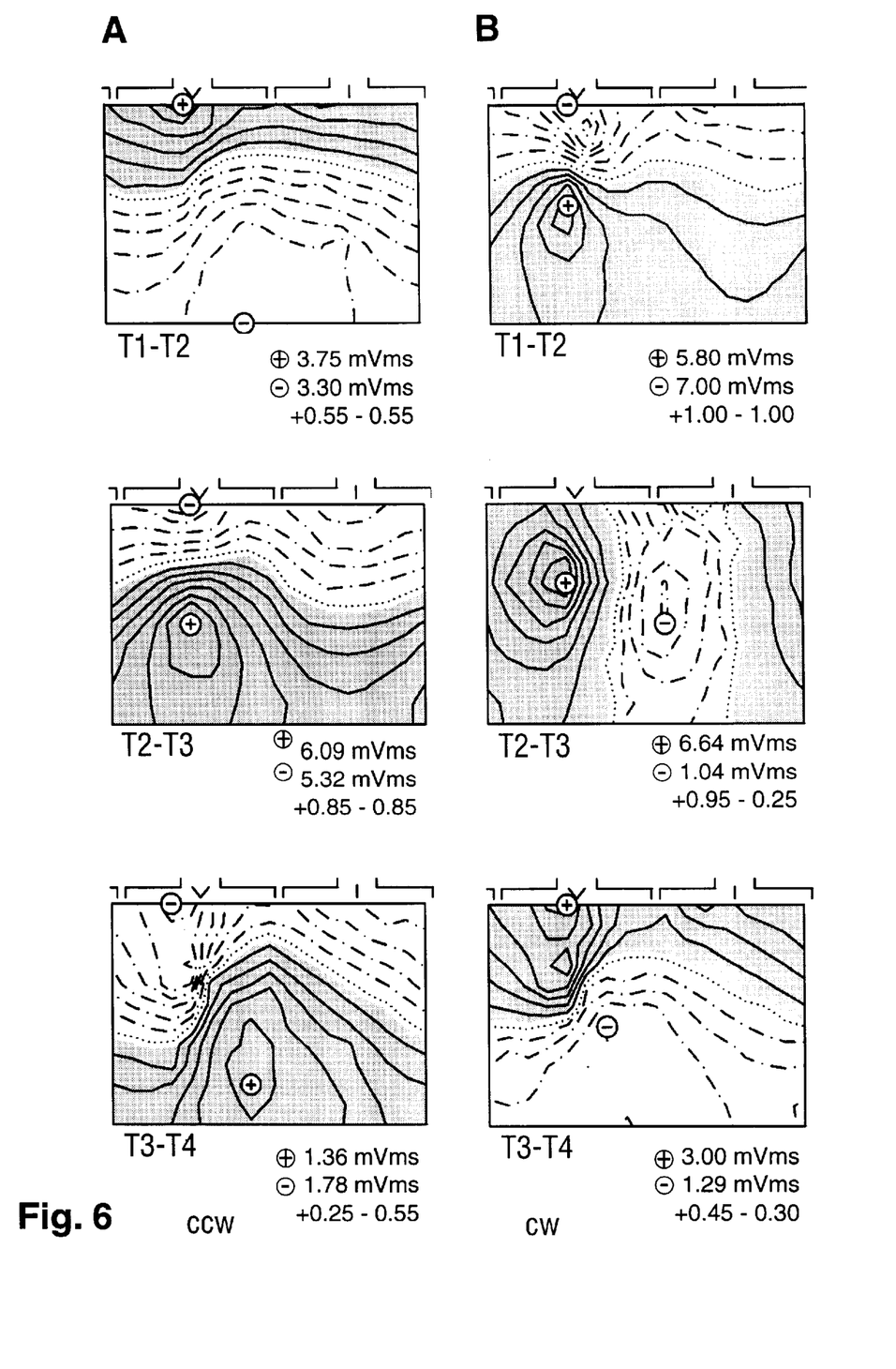
FIG. 6 depicts mean body surface integral maps of CCW (A) and CW (B) typical atrial flutter showing the stereotypical dipolar map patterns during three successive time intervals of the flutter wave cycle in each direction of rotation according to an embodiment of the present invention.

FIG. 6, depicts sets of mean body surface integral maps of CCW (A) and CW (B) typical atrial flutter. The CCW and CW maps show distinct differences of their stereotypical dipolar map patterns during three successive time intervals of the flutter wave cycle (T1–T2; T2–T3; T3–T4) in each direction of rotation.

Referring to FIG. 2, such mean maps are computed at step 36 from a group of typical (CCW and CW) and atypical flutter wave integral maps obtained in different patients.

The mean flutter wave data maps of typical (CCW and CW) and atypical atrial flutter are then stored in reference databases 38, 40. Database 38 contains maps of typical atrial flutter. Database 38 may be broken down into two sub-databases 38A, 38B, which contain mean flutter wave maps characteristic of CCW and CW atrial flutter, respectively. Database 40 contains mean flutter wave maps characteristic of atypical atrial flutter.

Mean body surface ECG integral maps of a given patient's atrial flutter 42 can subsequently be compared at step 44 to the reference database 38, 40 to detect and classify that patient's atrial flutter. Consequently, a unique database is available for improved detection and classification of typical and atypical atrial flutter.

Figure 7:
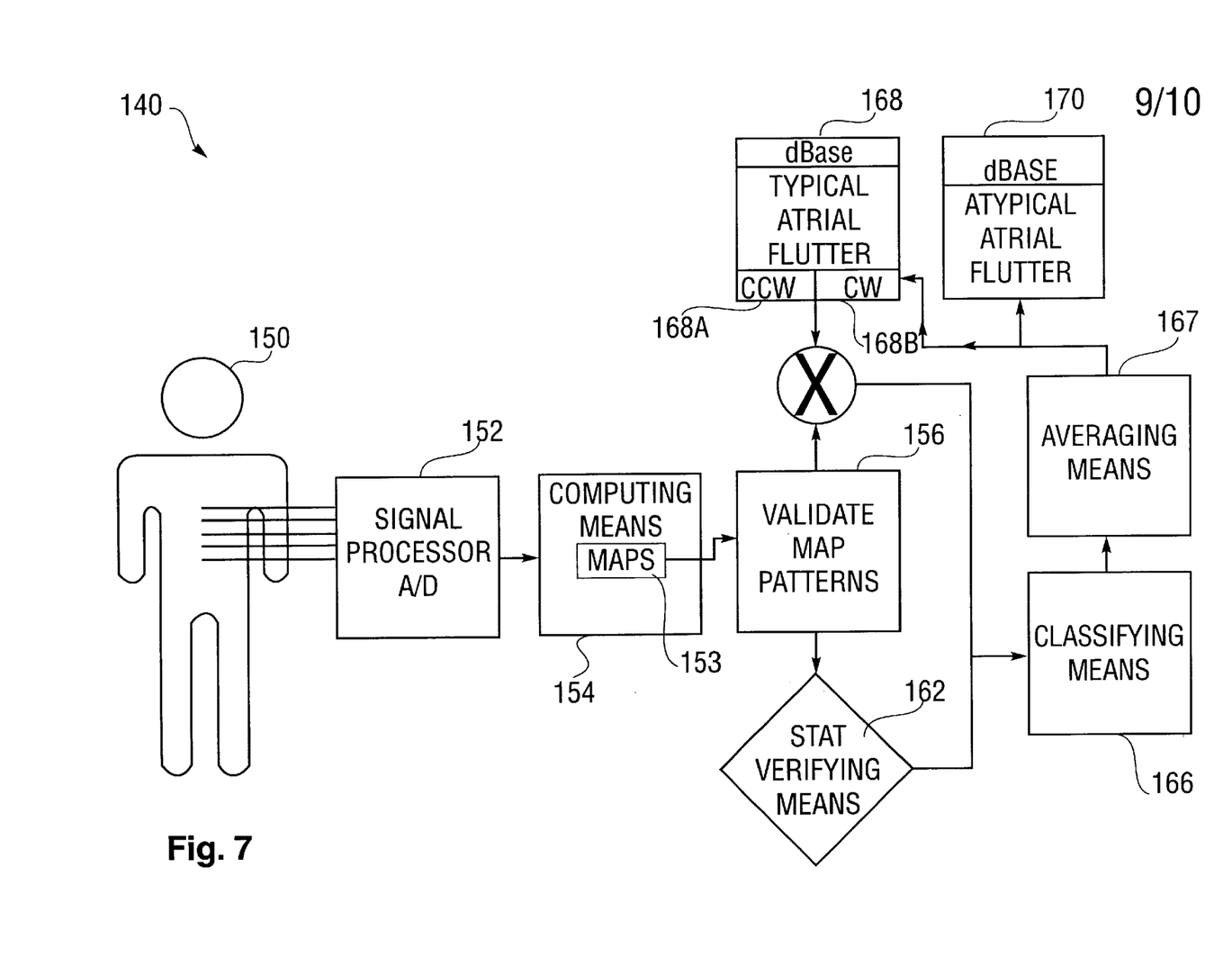
FIG. 7 depicts the design of an apparatus for classifying typical atrial flutter according to an embodiment of the present invention.

Referring to FIG. 7, the design of an apparatus 140 for classifying atrial flutter is described. The apparatus 140 obtains data for development of a database by recording unipolar or bipolar ECG tracings from a plurality of predetermined torso sites on a subject 150. In a preferred embodiment, the tracings are obtained from an array of 62 electrodes during spontaneous or induced atrial flutter. Alternatively, a smaller or larger number of electrodes or a different distribution of electrodes on the torso can also be used.

Electrocardiographic data from the electrodes are received by a signal processor 152. The electrocardiographic data may be acquired simultaneously by the signal processor 152 at a 1000 Hz sampling rate using a multi-lead ECG recording system. Alternatively, the signal processor can perform sequential sampling. Other data rates may also be used. The data can be upsampled using multirate filter banks when a lower sampling rate is used. The signal processor 152 may delete absent signals due to electrode obscurement by defibrillator patches or lead dislodgment. The signal processor 152 may automatically identify and reject poor quality signals. Alternatively, poor quality signals may be visually identified and rejected. These rejected signals may be substituted by interpolating adjacent lead recordings. The signal processor may also correct for interelectrode offset differences and linear baseline drift, e.g., using linear interpolation after selecting an isoelectric time instant or interval (other techniques for baseline adjustment can also be used). Due to the absence of a true isoelectric period in the flutter wave cycle, an interval is selected in the signal near to the zero voltage level directly preceding the negative inscription of the flutter wave. The signal processor 152 may incorporate digital filtering to remove line frequency interference when necessary, e.g., with a 60-Hz notch filter (other types of filter or means of filtering may also be used).

A computing means 154 coupled to the signal processor 152 computes series of maps 153, e.g., potential maps, of the entire flutter wave cycle, e.g., at 2-ms intervals (other intervals can also be used). The potential maps are visually evaluated to determine flutter wave onset and offset as the point in time when one of the extreme values supersedes and returns within a 30 $\mu$V reference voltage window around the zero line. Alternatively, other criteria for flutter wave onset and offset can also be used. The electrocardiographic data are analyzed qualitatively by inspecting the temporal changes in voltage distribution throughout the flutter wave cycle in each map 153. Distinct periods within the flutter wave cycle are identified at which stable voltage distributions occur for a time interval of at least 20 ms. In a particular embodiment, integral maps 153 of selected time intervals in the flutter wave cycle are computed for each time interval. As an alternative, the computing means 154 may compute flutter wave potential maps at selected time intervals, e.g., at one or more peaks in the flutter wave. The computing means 154 may include software or hardware or some combination of both. Furthermore, the computing means may be incorporated into signal processor 152.

A validating means 156 then validates the patterns in the maps 153. The validating means typically includes circuitry or software for waveform analysis or filtering to determine if a given map pattern makes sense. For example, the validating means may reject any map for which the integral or potential values lie outside of a predetermined range. Alternatively, the validating means 156 may display the map for visual inspection by an expert. The apparatus 140 may optionally include a verifying means 162. The verifying means 162 performs statistical analysis on the map patterns in the maps 153 to determine if the map patterns lie within a statistical margin for error. The verifying means 162 may be part of the signal processor 152 or a separate unit. The verifying means may be implemented in software or hardware or some combination of both.

Verification of the presence of CCW or CW typical atrial flutter may be attained using multipolar endocardial catheter recordings in the right atrium, the coronary sinus and possibly the left atrium. The presence of CCW or CW typical atrial flutter is confirmed by the characteristic sequence of endocardial activation and the demonstration of concealed entrainment with pacing in the subeustachian isthmus (other methods to confirm the flutter type and direction of rotation can also be used).

A classifying means 166 classifies the validated map patterns obtained from the subject 150 as CCW or CW typical atrial flutter according to definition and comparison with endocardial catheter recordings. Once the maps 153 have been classified as CCW typical atrial flutter, CW typical atrial flutter, or atypical atrial flutter, an averaging means 167 averages the atrial flutter maps 153 that lie in the same classification. The computing means 154, verifying means 162, classifying means 166 and averaging means 167 may be in the form of modules implemented in hardware, firmware, software, and or a combination thereof. The mean maps are then stored in the reference databases 168, 170, using a combining module, e.g., the classifying means 166, the averaging means 167 or some combination thereof. The databases 168, 170 have features in common with databases 38, 40 described above with respect to FIG. 2. For example, database 168 stores mean flutter wave maps (e.g., potential maps or integral maps) of typical CCW 168A and CW 168B body surface ECG atrial flutter waves. Database 170 stores mean flutter wave maps (e.g., potential map or integral map) of atypical body surface ECG atrial flutter waves.

Classified map patterns from a plurality of subjects 150 build up the databases 168, 170. Once the databases contain a sufficient number of map patterns, the apparatus 140 may be used to diagnose and classify atrial flutter in a patient (not shown) by comparing map patterns from the patient to the map patterns in the databases 168, 170.

Figure 8:
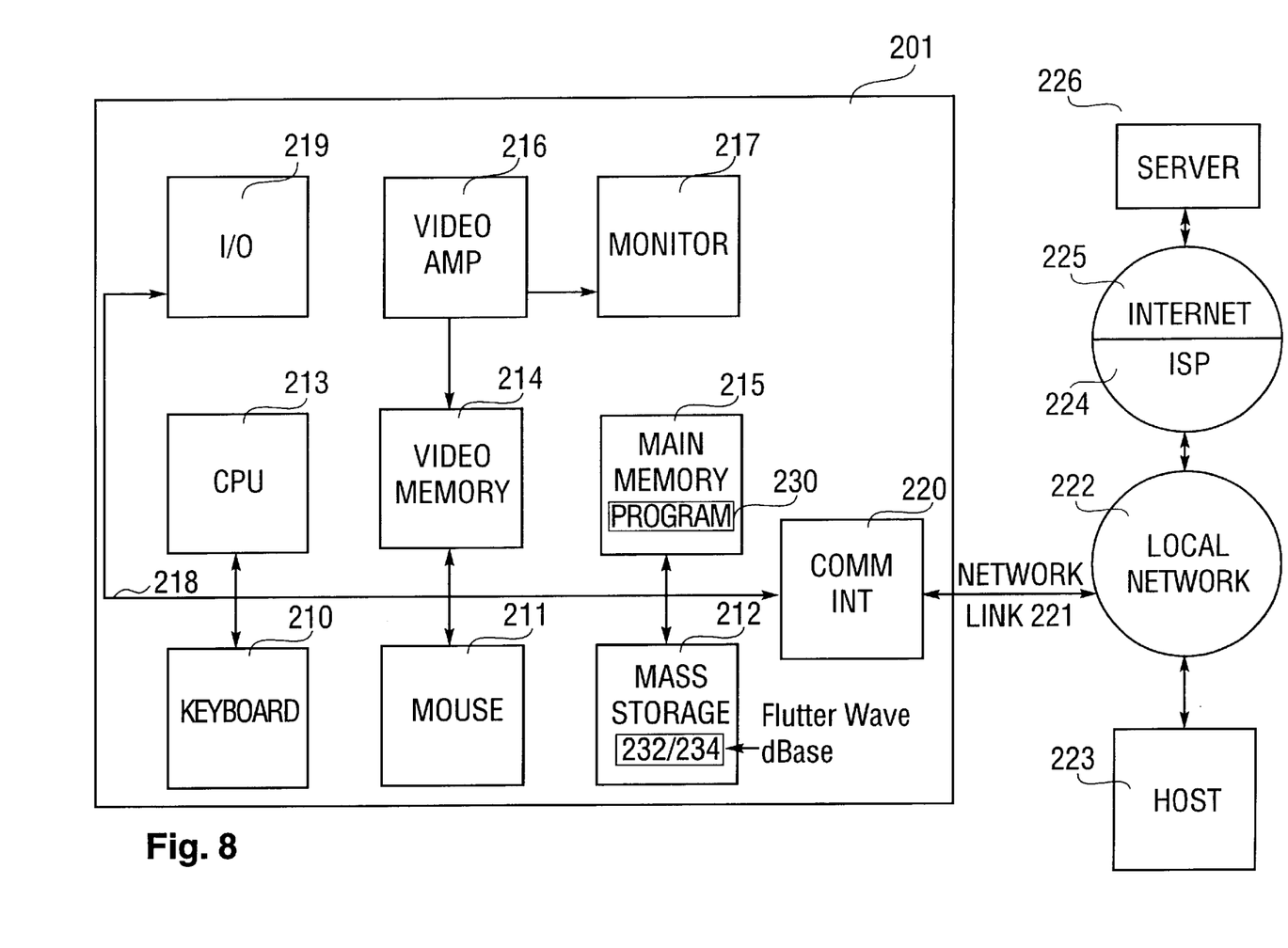
FIG. 8 depicts a block diagram of storing a database of mean body surface ECG flutter wave data map patterns in a computer-readable medium for retrieval, analysis and sharing according to an embodiment of the present invention.

Referring to FIG. 8, an embodiment of the invention can be implemented as computer software in the form of computer readable code executed on a general purpose computer such as computer 201, or in the form of bytecode class files running on such a computer. A keyboard 210 and a mouse 211 are coupled to a bi-directional system bus 218. The keyboard and mouse are for introducing user input to the computer system and communicating that user input to processor 213. Other suitable input devices may be used in addition to, or in place of, the mouse 211 and keyboard 210. I/O (input/output) unit 219 coupled to bidirectional system bus 218 represents such I/O elements as a printer, A/V (audio/video), I/O, etc.

Computer 201 includes a video memory 214, main memory 215 and mass storage 212 (database storage), all coupled to bi-directional system bus 218 along with keyboard 210, mouse 211 and processor 213. The mass storage 212 may include both fixed and removable media, such as magnetic, optical or magnetic optical storage systems or any other available mass storage technology. Bus 218 may contain, for example, thirty-two address lines for addressing video memory 214 or main memory 215. The system bus 218 also includes, for example, a 32-bit data bus for transferring data between and among the components, such as processor 213, main memory 215, video memory 214 and mass storage 212. Alternatively, multiplex data/address lines may be used instead of separate data and address lines.

In an embodiment of the invention, any suitable microprocessor or microcomputer may be utilized as processor 213. Main memory 215 may be a random access memory (RAM), dynamic random access memory (DRAM) or an equivalent. The main memory 215 typically contains a program 230 having instructions executable by the processor 213. In a preferred embodiment, the program 230 contains processor executable instructions that implement the steps of the method 1 of FIG. 1 or method 21 of FIG. 2. Alternatively, the program 230 may be stored wholly or partly in the mass storage 212. The mass storage 212 may contain databases 232, 234 of mean atrial flutter wave maps for use with the program 230. The databases may have features on common with the databases 38, 40 described above with respect to FIG. 2 and/or databases 168, 170 of FIG. 7. For example, database 232 may contain mean atrial flutter wave maps characteristic of CCW and CW typical atrial flutter. Similarly, database 234 may contain mean atrial flutter wave maps characteristic of atypical atrial flutter. Alternatively, databases 232, 234 may be stored wholly or partly in main memory 215.

Video memory 214 may be a dual-ported video random access memory. One port of the video memory 214 is coupled to video amplifier 216. The video amplifier 216 is used to drive the display 217 (i.e. CRT, LCD). The video amplifier and the monitor may be implemented by any suitable apparatus.

Computer 201 may also include a communication interface 220 coupled to bus 218. Communication interface 220 provides a two-way data communication coupling via a network link 221 to a local network 222. For example, if communication interface 220 is an integrated services digital network (ISDN) card or a modem, communication interface 220 provides a data communication connection to the corresponding type of telephone line, which comprises part of network link 221. If communication interface 220 is a local area network (LAN) card, communication interface 220 provides a data communication connection via network link 221 to a compatible LAN. Wireless links are also possible. In any such implementation, communication interface 220 sends and receives electrical, electromagnetic or optical signals that carry digital data streams representing various types of information.

Network link 221 typically provides data communication through one or more networks to other data devices. For example, network link 221 may provide a connection through local network 222 to a local server computer or host 223 or to data equipment operated by an Internet Service Provider (ISP) 224. ISP 224 in turn provides data communication services through the world wide packet data communication network now commonly referred to as the "Internet" 225. Local network 222 and Internet 225 both use electrical, electromagnetic or optical signals that carry digital data streams. The signals through the various networks and the signals on network link 221 and through communication interface 220, which carry the digital data to and from computer 201, are exemplary forms of carrier waves transporting the information.

Computer 201 can send messages and receive data, including program code, through the network(s), network link 221, and communication interface 220. In the Internet example, remote server computer 226 might transmit a requested code for an application program or specific electrocardiography database through Internet 225, ISP 224, local network 222 and communication interface 220. Consequently, they provide an important link for rapid medical information exchange such as telemedicine.

The received code may be executed by processor 213 as it is received, and/or stored in mass storage 212, or other non-volatile storage for later execution. In this manner, computer 201 may obtain application code in the form of a carrier wave.

Application code (i.e. database, procedures, etc.) may be embodied in any form of computer program product. A computer program product comprises a medium configured to store or transport computer readable code, or in which computer readable code may be embedded. Some examples of computer program products are CD-ROM disks, ROM cards, floppy disks, magnetic tapes, computer hard drives, servers on a network, and carrier waves.

The computer systems described are for purposes of example only. An embodiment of the invention may be implemented in any type of computer system or programming or processing environment.

The ability to rapidly acquire, store, analyze and share medical information is necessary considering the rapid rate of change in medical technology. This computer 201 embodiment provides a database system capable of acquiring, analyzing, displaying and storing patient data in real time locally. In addition, communicating with other medical research centers allows sharing of medical information which can add new techniques and enlarge the subject database by the addition of new data elements from other centers.

It will be clear to one skilled in the art that the above embodiment may be altered in many ways without departing from the scope of the invention. Accordingly, the scope of the invention should be determined by the following claims and their legal equivalents.

What is claimed is:

1. A system for developing a database of body surface ECG flutter wave data for classification of atrial flutter wherein said database is derived from data of two or more subjects comprising:
   a) means for generating atrial flutter data;
   b) means for receiving the data from a subject;
   c) means for classifying the data as typical counterclockwise (CCW), typical clockwise (CW), or atypical atrial flutter;
   d) means for averaging the classified data; and
   e) means for storing and accessing the averaged data in the database.

2. The system as set forth in claim 1, wherein the flutter wave data are in the form of flutter wave maps.

3. The system as set forth in claim 1, further comprising means for inducing said atrial flutter by electrically stimulating an arrhythmogenic substrate of an atrium of the subject using a probe.

4. The system as set forth in claim 1, wherein the receiving means comprises means for sensing heart cycle signals wherein said subject is spontaneously producing said atrial flutter or wherein said atrial flutter is being induced.

5. The system as set forth in claim 4, wherein the receiving means comprises means for detecting a heart cycle signal with a plurality of sensors proximate a subject's torso.

6. The system as set forth in claim 4, wherein the receiving means comprises means for separating from said heart signal an atrial signal obscured by a ventricular signal.

7. The system as set forth in claim 6, wherein the receiving means comprises means for selecting at least one reference cycle from among a plurality of heart cycles to determine said atrial flutter.

8. The system as set forth in claim 7, wherein the receiving means comprises means for selecting time intervals of the reference cycle and comparing signals from a plurality of sensors during said selected time intervals.

9. The system as set forth in claim 8, wherein the receiving means comprises means for generating a data matrix by integrating the separated signals from associated sensor locations within said selected time intervals to define one or more integral values, and arranging the integral values within the matrix according to locations of said associated sensor locations along a surface of a subject's torso.

10. The system as set forth in claim 9, wherein the receiving means comprises means for computing integral maps over selected time intervals with stable voltage and plotting said data matrix.

11. The system as set forth in claim 10, wherein the computing means comprises means for determining lines of constant integral values, and identifying characteristic body surface maps of said atrial flutter using the lines of constant integral values mapped upon representations of a surface of the subject's torso.

12. The system as set forth in claim 10, wherein the computing means comprises means for representing different integral values by one or more different colors mapped upon representations of a surface of the subject's torso.

13. The system set forth in claim 8, wherein the receiving means comprises means for generating a data matrix of potential signals from associated sensor locations within said selected time intervals to define one or more potential values, and arranging the potential values within the matrix according to said locations of said associated sensor locations along a body surface of a torso.

14. The system as set forth in claim 13, wherein said generating means comprises means for determining lines of constant potential values, and identifying characteristic body surface maps of said atrial flutter using the lines of constant potential values mapped upon representations of a surface of a subject's torso.

15. The system as set forth in claim 13, wherein said generating means comprises means for representing different potential values by one or more different colors mapped upon representations of a surface of a subject's torso.

16. The system as set forth in claim 1, wherein the classifying means comprises means for determining characteristic body surface maps specific to CCW or CW typical or atypical atrial flutter data.

17. The system as set forth in claim 16 wherein the classifying means comprises means for defining said CCW typical flutter data as a right atrial arrhythmia characterized by CCW wavefront rotation around a tricuspid annulus and critical dependence on a subeustachian isthmus.

18. The system as set forth in claim 16, wherein the classifying means comprises means for defining said CW typical flutter data as a right atrial arrhythmia characterized by CW wavefront rotation around a tricuspid annulus and critical dependence on a subeustachian isthmus.

19. The system as set forth in claim 16, wherein the classifying means comprises means for verifying said CCW or CW typical flutter data.

20. The system as set forth in claim 19, wherein the verifying means comprises means for using multipolar endocardial catheter recordings from a right atrium and/or coronary sinus to demonstrate characteristic said flutter rotation and critical dependence.

21. The system as set forth in claim 19, wherein the verifying means comprises means for evaluating intersubject comparability of said atrial flutter data with the same direction of rotation.

22. The system of claim 21 wherein the verifying means further comprises means for computing correlation coefficients between maps to validate use of subject data.

23. The system as set forth in claim 21, wherein the averaging means comprises means for calculating mean maps from verified atrial flutter data maps to construct a database of characteristic body surface ECG flutter wave maps.

24. The system as set forth in claim 23, wherein said means for calculating mean maps comprises means for comparing and differentiating CCW flutter wave rotation from CW flutter wave rotation.

25. The system as set forth in claim 1, wherein the storing means comprises means for using a computer to store, search and analyze said averaged data.

26. The system as set forth in claim 25, wherein the storing means comprises means for using said computer to detect and classify typical or isthmus-dependent atrial flutter.

27. A method for developing a database of body surface ECG flutter wave data for classification of atrial flutter wherein said database is derived from data of two or more subjects comprising the steps of:
   a) receiving atrial wave flutter data from the subjects;
   b) classifying the data as typical counterclockwise (CCW) or clockwise (CW) and atypical atrial flutter;
   c) averaging the classified data; and
   d) storing and accessing the averaged data in the database.

28. The method as set forth in claim 27, wherein the flutter wave data are flutter wave maps.

29. The method as set forth in claim 28, wherein the developing method comprises inducing said atrial flutter by electrically stimulating an arrhythmogenic substrate of an atrium of the subject using a probe.

30. The method as set forth in claim 27, wherein the receiving method comprises sensing heart cycle signals wherein said subject is spontaneously producing said atrial flutter or wherein said atrial flutter is being induced.

31. The method as set forth in claim 30, wherein the receiving method comprises detecting a heart cycle signal with a plurality of sensors proximate a subject's torso.

32. The method as set forth in claim 30, wherein the receiving step comprises separating from said heart signal an atrial signal obscured by a ventricular signal.

33. The method as set forth in claim 32, wherein the receiving step further comprises selecting at least one reference cycle from among a plurality of heart cycles to determine said atrial flutter.

34. The method as set forth in claim 33, wherein the receiving step further comprises selecting time intervals of the reference cycle and comparing signals from a plurality of sensors during said selected time intervals.

35. The method as set forth in claim 34, wherein the receiving step comprises generating a data matrix by integrating the separated signals from associated sensor locations within said selected time intervals to define an integral value, and arranging the integral values within the matrix according to locations of said associated sensor locations along a body surface of a torso.

36. The method as set forth in claim 35, wherein the receiving step comprises computing integral maps over selected time intervals with stable voltage and plotting said data matrix.

37. The method as set forth in claim 36, wherein the integral maps are computed by determining lines of constant integral values along the plots, and identifying characteristic body surface maps of said atrial flutter using the lines of constant integral values mapped upon representations of surface of the subject's torso.

38. The method of claim 36, wherein the integral maps represent different integral values by one or more different colors mapped upon representations of a surface of the subject's torso.

39. The method of claim 34, wherein the receiving step comprises generating a data matrix of potential signals from associated sensor locations within said selected time intervals to define one or more potential values, and arranging the potential values within the matrix according to said locations of said associated sensor locations along a body surface of a torso.

40. The method of claim 39, wherein the generating step comprises determining lines of constant potential values, and identifying characteristic body surface maps of said atrial flutter using the lines of constant potential values mapped upon representations of a surface of a subject's torso.

41. The method of claim 39, wherein the generating step comprises representing different potential values by one or more different colors mapped upon representations of a surface of a subject's torso.

42. The method as set forth in claim 27, wherein the classifying method comprises determining characteristic body surface maps specific to CCW or CW typical or atypical atrial flutter data.

43. The method as set forth in claim 42, wherein the classifying method comprises defining said CCW typical flutter data as a right atrial arrhythmia characterized by CCW wavefront rotation around a tricuspid annulus and critical dependence on a subeustachian isthmus.

44. The method as set forth in claim 42, wherein the classifying method comprises defining said CW typical flutter data as a right atrial arrhythmia characterized by CW wavefront rotation around a tricuspid annulus and critical dependence on a subeustachian isthmus.

45. The method as set forth in claim 42, wherein the classifying method comprises verifying said CCW or CW typical flutter data.

46. The method as set forth in claim 45, wherein the verifying method comprises using multipolar endocardial catheter recordings from a right atrium and/or coronary sinus to demonstrate characteristic flutter rotation and critical dependence.

47. The method as set forth in claim 45, wherein the verifying method comprises evaluating intersubject comparability of said atrial flutter data with the same direction of rotation.

48. The method of claim 47 further comprising computing correlation coefficients between said body surface maps to validate use of subject data.

49. The method as set forth in claim 27, wherein the averaging method comprises calculating mean maps from said atrial flutter data to construct a database of characteristic said body surface ECG flutter wave maps.

50. The method as set forth in claim 49, wherein the method of developing said database comprises comparing and differentiating CCW flutter wave rotation from CW flutter wave rotation.

51. The method as set forth in claim 27, wherein the storing method comprises using a computer to store, search and analyze said averaged data.

52. The method as set forth in claim 51, wherein the storing method comprises using said computer to detect and classify typical or isthmus-dependent atrial flutter.

53. An apparatus for classifying typical or isthmus-dependent and atypical atrial flutter, comprising:
   a) a signal processor means for receiving electrical signals indicative of a heart's electrical activity from a plurality of torso sites;
   b) a QRST subtraction means for removing ventricular activity superimposed on the atrial activity from said electrical signals, and for outputting an atrial flutter baseline signal;
   c) a means for receiving said baseline signal to classify said atrial flutter as CCW typical, CW typical or atypical atrial flutter, wherein the atrial flutter is classified based on a comparison of said baseline signal to a database of mean CCW typical, CW typical or atypical body surface ECG flutter wave data map patterns; and
   d) transformation means for graphically representing averaged atrial flutter data obtained from said baseline signal, on a torso representation of a subject.

54. A system for developing an arrhythmia database from a plurality of subjects, the system comprising:
   a) at least one sensor array coupleable to the subject, said at least one sensor array transmitting atrial flutter data in response to an atrial flutter of the subject;
   b) a processor receiving said atrial flutter data from said sensor array;
   c) a classification module reciving said atrial flutter data from said processor, the classification module classifying said atrial flutter as typical counterclockwise, typical clockwise, or atypical; and
   d) a combining module that combines said atrial flutter data with said database according to the classification of said atrial flutter data.

* * * * *